US012661016B2

(12) United States Patent
Kaneko et al.

(10) Patent No.: US 12,661,016 B2
(45) Date of Patent: Jun. 23, 2026

(54) MEASUREMENT SYSTEM, MEASUREMENT METHOD, AND MEASUREMENT PROGRAM

(71) Applicant: FUJIFILM CORPORATION, Tokyo (JP)

(72) Inventors: Yasuhisa Kaneko, Kanagawa (JP); Tomohide Hiragami, Kanagawa (JP); Kenji Nagamiya, Kanagawa (JP); Nobuya Kitamura, Kanagawa (JP); Yasuyuki Hosono, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 978 days.

(21) Appl. No.: 17/662,232

(22) Filed: May 6, 2022

(65) Prior Publication Data

US 2022/0378296 A1    Dec. 1, 2022

(30) Foreign Application Priority Data

May 25, 2021    (JP) ................................. 2021-087936

(51) Int. Cl.
*A61B 5/0205*          (2006.01)
*A61B 5/00*            (2006.01)
(Continued)

(52) U.S. Cl.
CPC ........... *A61B 5/0205* (2013.01); *A61B 5/021* (2013.01); *A61B 5/14551* (2013.01); *A61B 5/6801* (2013.01)

(58) Field of Classification Search
CPC .............. A61B 5/1455; A61B 5/14551; A61B 5/14552; A61B 5/0205; A61B 5/021; A61B 5/6801; A61B 5/7285
See application file for complete search history.

(56) References Cited

U.S. PATENT DOCUMENTS

| | | | | |
|---|---|---|---|---|
| 5,515,847 A | * | 5/1996 | Braig ................. | A61B 5/14532 |
| | | | | 600/316 |
| 8,457,707 B2 | * | 6/2013 | Kiani ................. | A61B 5/14551 |
| | | | | 600/323 |

(Continued)

FOREIGN PATENT DOCUMENTS

| | | |
|---|---|---|
| JP | 2012-528696 A | 11/2012 |
| JP | 2017-142580 A | 8/2017 |

(Continued)

OTHER PUBLICATIONS

English language translation of the following: Office action dated Nov. 26, 2024 from the JPO in a Japanese patent application No. 2021-087936 corresponding to the instant patent application. This office action translation is submitted now in order to supplement the understanding of the cited references which are being disclosed in the instant Information Disclosure Statement.

(Continued)

*Primary Examiner* — Eric F Winakur
(74) *Attorney, Agent, or Firm* — SOLARIS Intellectual Property Group, PLLC

(57) ABSTRACT

A measurement system comprising: a first measurement apparatus including at least a first processor; and a second measurement apparatus including at least a second processor, wherein the first processor and the second processor are configured to measure biological information of a user by synchronizing a timing with each other.

8 Claims, 6 Drawing Sheets

(51) Int. Cl.
  A61B 5/021        (2006.01)
  A61B 5/1455       (2006.01)

(56)                    References Cited

U.S. PATENT DOCUMENTS

| | | | |
|---|---|---|---|
| 2010/0312079 A1 | 12/2010 | Larsen et al. | |
| 2017/0231508 A1* | 8/2017 | Edwards | A61B 5/02055 |
| | | | 600/301 |
| 2020/0187809 A1 | 6/2020 | Larsen et al. | |
| 2020/0353239 A1 | 11/2020 | Daniels et al. | |
| 2020/0405171 A1 | 12/2020 | Wei | |
| 2021/0386300 A1* | 12/2021 | Rogers | A61B 5/02055 |
| 2022/0330885 A1* | 10/2022 | Xu | A61B 5/02055 |

FOREIGN PATENT DOCUMENTS

| | | | |
|---|---|---|---|
| JP | 2020-516327 A | 6/2020 |
| JP | 2020-142070 A | 9/2020 |
| WO | 2019/163028 A1 | 8/2019 |

OTHER PUBLICATIONS

English language translation of the following: Decision of Refusal dated May 7, 2025 from the JPO in a Japanese patent application No. 2021-087936 corresponding to the instant patent application.

* cited by examiner

FIG. 2

| PART ON WHICH EACH MEASUREMENT APPARATUS IS MOUNTED | EXAMPLE OF FORM OF EACH MEASUREMENT APPARATUS | MEASUREMENT TARGET PART OF BIOLOGICAL INFORMATION |
|---|---|---|
| RIGHT EAR AND LEFT EAR | EARPHONE TYPE AND GLASSES TYPE | RIGHT AND LEFT EXTERNAL CAROTID ARTERIES |
| RIGHT SIDE AND LEFT SIDE OF HEAD | HEAD SUPPORTER TYPE, HEAD MASSAGER TYPE, PILLOW TYPE | RIGHT AND LEFT EXTERNAL CAROTID ARTERIES OR COMMON CAROTID ARTERIES |
| UPPER PORTION AND LOWER PORTION OF HEAD | | EXTERNAL CAROTID ARTERY AND COMMON CAROTID ARTERY |
| UPPER RIGHT PORTION, LOWER RIGHT PORTION, UPPER LEFT PORTION, AND LOWER LEFT PORTION OF HEAD | | RIGHT AND LEFT EXTERNAL CAROTID ARTERIES AND COMMON CAROTID ARTERIES |
| RIGHT KNEE AND LEFT KNEE | KNEE SUPPORTER TYPE, PANTS TYPE, CHAIR TYPE | RIGHT AND LEFT FEMORAL ARTERIES |
| RIGHT LEG AND LEFT LEG | | RIGHT AND LEFT ANTERIOR TIBIAL ARTERIES OR POSTERIOR TIBIAL ARTERIES |
| UPPER PORTION OF RIGHT LEG, LOWER PORTION OF RIGHT LEG, UPPER PORTION OF LEFT LEG, AND LOWER PORTION OF LEFT LEG | | RIGHT AND LEFT ANTERIOR TIBIAL ARTERIES AND POSTERIOR TIBIAL ARTERIES |
| KNEECAP AND POPLITEUS (SAME SIDE) | | ANTERIOR TIBIAL ARTERY AND POSTERIOR TIBIAL ARTERY |
| INSTEP AND ANKLE (SAME SIDE) | ANKLE SUPPORTER TYPE | FEMORAL VEIN AND POSTERIOR TIBIAL VEIN / ANTERIOR TIBIAL ARTERY AND POSTERIOR TIBIAL ARTERY |
| RIGHT INSTEP, LEFT INSTEP, RIGHT ANKLE, AND LEFT ANKLE | | RIGHT AND LEFT ANTERIOR TIBIAL ARTERIES AND POSTERIOR TIBIAL ARTERIES |
| RIGHT INSTEP AND LEFT ARM | ANKLE SUPPORTER TYPE AND WRISTWATCH TYPE | RIGHT POSTERIOR TIBIAL ARTERY AND LEFT BRACHIAL ARTERY |
| RIGHT EAR, LEFT EAR, AND SINGLE ARM | EARPHONE TYPE, GLASSES TYPE, AND WRISTWATCH TYPE | RIGHT AND LEFT EXTERNAL CAROTID ARTERIES AND BRACHIAL ARTERIES |
| RIGHT SIDE AND LEFT SIDE OF HEAD, RIGHT ARM, AND LEFT ARM | TURTLENECK WEAR TYPE | RIGHT AND LEFT EXTERNAL CAROTID ARTERIES AND BRACHIAL ARTERIES |
| RIGHT KNEE, LEFT KNEE, RIGHT ANKLE, AND LEFT ANKLE | PANTS TYPE, KNEE SUPPORTER TYPE, ANKLE SUPPORTER TYPE, CHAIR TYPE | RIGHT AND LEFT FEMORAL ARTERIES AND POSTERIOR TIBIAL ARTERIES |
| HIP JOINT OF RIGHT LEG, KNEECAP, FRONT SIDE AND REAR SIDE OF ANKLE AND HIP JOINT OF LEFT LEG, KNEECAP, AND FRONT SIDE AND REAR SIDE OF ANKLE | | RIGHT AND LEFT FEMORAL VEINS, ANTERIOR TIBIAL VEINS, AND POSTERIOR TIBIAL VEINS |

FIG. 5

PATTERN 1
　　FIRST MEASUREMENT APPARATUS
　　SECOND MEASUREMENT APPARATUS

PATTERN 2
　　FIRST MEASUREMENT APPARATUS
　　SECOND MEASUREMENT APPARATUS

PATTERN 3
　　FIRST MEASUREMENT APPARATUS
　　SECOND MEASUREMENT APPARATUS

PATTERN 4
　　FIRST MEASUREMENT APPARATUS
　　SECOND MEASUREMENT APPARATUS

PATTERN 5
　　FIRST MEASUREMENT APPARATUS
　　SECOND MEASUREMENT APPARATUS

PATTERN 6
　　FIRST MEASUREMENT APPARATUS
　　SECOND MEASUREMENT APPARATUS

PATTERN 7
　　FIRST MEASUREMENT APPARATUS
　　SECOND MEASUREMENT APPARATUS

PATTERN 8
　　FIRST MEASUREMENT APPARATUS
　　SECOND MEASUREMENT APPARATUS

PATTERN 9
　　FIRST MEASUREMENT APPARATUS
　　SECOND MEASUREMENT APPARATUS

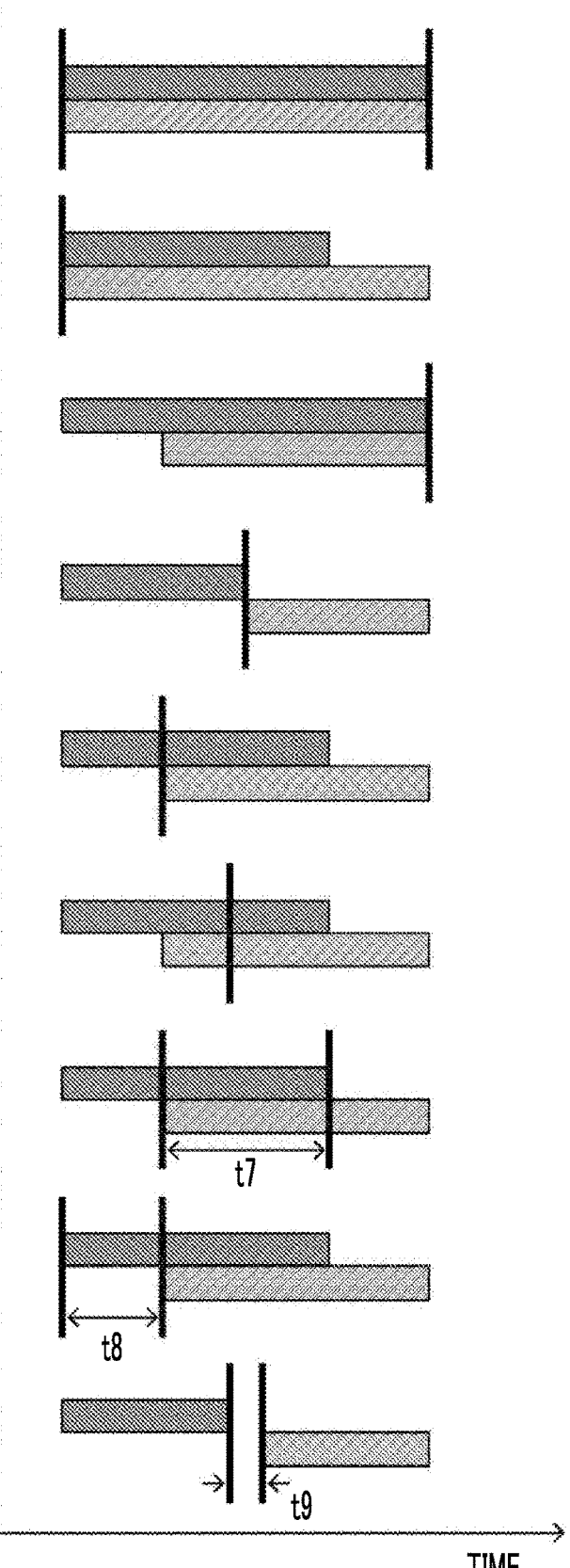

TIME

MEASUREMENT SYSTEM, MEASUREMENT METHOD, AND MEASUREMENT PROGRAM

CROSS-REFERENCE TO RELATED APPLICATIONS

The present application claims priority under 35 U.S.C. § 119 to Japanese Patent Application No. 2021-087936, filed on May 25, 2021. The above application is hereby expressly incorporated by reference, in its entirety, into the present application.

BACKGROUND

Technical Field

The present disclosure relates to a measurement system, a measurement method, and a measurement program.

Related Art

In the related art, a technology for measuring biological information from a plurality of parts of a body of a user using a wearable device and the like has been known. For example, JP2020-516327A discloses monitoring a heart pulse, an arterial blood oxygen saturation level, and the like by embedding at least one sensor in clothes. In addition, for example, WO2019/163028A discloses taking an electrocardiogram of a user sitting in a chair by providing an electrode for electrocardiogram measurement in each of an armrest portion and a footrest portion of the chair.

In recent years, a technology enabling an abnormality that is difficult to be discovered with only biological information measured from one location to be found by measuring the biological information from a plurality of different locations and performing a comprehensive diagnosis based on a measurement result has been expected. However, the measurement result of the biological information reflects states of various diseases and thus, is considered to change depending on a timing of measurement. Therefore, in a case of measuring the biological information from the plurality of different locations and using the biological information in the diagnosis, it is desired to improve accuracy of the diagnosis by synchronizing the timing of measuring the biological information in each location.

SUMMARY

The present disclosure provides a measurement system, a measurement method, and a measurement program that can improve accuracy of a diagnosis.

A first aspect of the present disclosure is a measurement system comprising a first measurement apparatus including at least a first processor, and a second measurement apparatus including at least a second processor, in which the first processor and the second processor are configured to measure biological information of a user by synchronizing a timing with each other.

In the first aspect, the first processor and the second processor may be configured to measure the biological information of the user by synchronizing the timing in at least a part of a measurement period of the biological information of the user with each other.

In the first aspect, the first processor and the second processor may be configured to measure the biological information of the user by synchronizing at least one of a start timing or an end timing of the measurement period with each other.

In the first aspect, the first processor and the second processor may be configured to measure the biological information of the user with a predetermined time difference from each other.

In the first aspect, each of the first processor and the second processor may be configured to measure the biological information in parts of left-right symmetry of a body of the user.

In the first aspect, each of the first processor and the second processor may be configured to measure the biological information in upstream and downstream sides of a blood vessel branch of the user.

In the first aspect, each of the first processor and the second processor may be configured to measure the biological information in at least one of an artery or a vein of the user.

In the first aspect, the biological information may be at least one of a pulse or an arterial blood oxygen saturation level.

In the first aspect, the first processor and the second processor may be configured to synchronize the timing with each other using wireless communication.

The measurement system according to the first aspect may further comprise a third measurement apparatus including at least a third processor, in which at least two out of the first processor, the second processor, and the third processor measure the biological information of the user by synchronizing the timing with each other.

A second aspect of the present disclosure is a measurement method executed by a computer, the method comprising measuring biological information of a user by causing a first measurement apparatus and a second measurement apparatus each measuring the biological information of the user to synchronize a timing with each other.

A third aspect of the present disclosure is a measurement program causing a computer to execute a process comprising measuring biological information of a user by causing a first measurement apparatus and a second measurement apparatus each measuring the biological information of the user to synchronize a timing with each other.

The measurement system, the measurement method, and the measurement program according to the aspects of the present disclosure can improve accuracy of a diagnosis.

BRIEF DESCRIPTION OF THE DRAWINGS

FIG. 2 is a diagram illustrating an example of a measurement target of biological information.

FIG. 5 is a specific example of a timing of synchronization.

DETAILED DESCRIPTION

Hereinafter, an embodiment of the disclosed technology will be described in detail with reference to the drawings.

Figure 1:
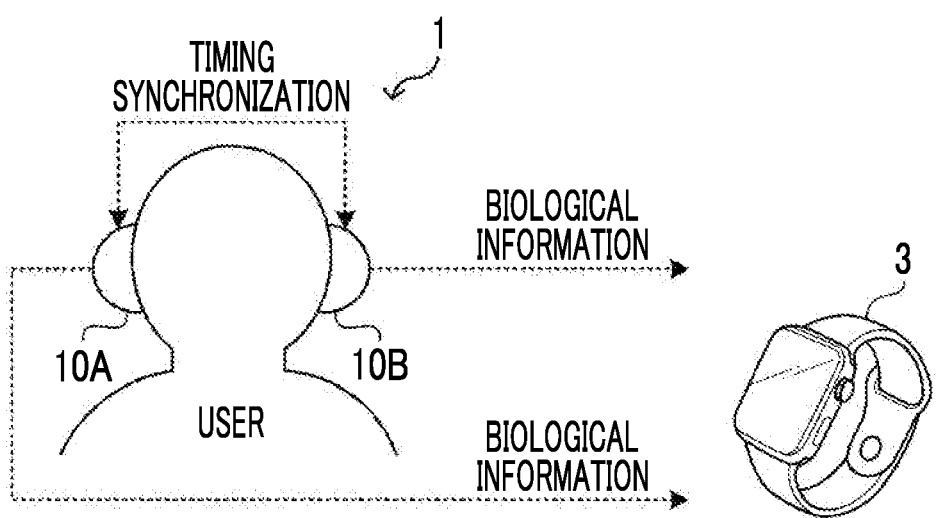
FIG. 1 is a schematic configuration diagram of a measurement system.

First, an example of a configuration of a measurement system 1 according to the present embodiment will be described with reference to FIG. 1. As illustrated in FIG. 1, the measurement system 1 comprises a first measurement apparatus 10A and a second measurement apparatus 10B. Each of the first measurement apparatus 10A and the second measurement apparatus 10B is mounted on different parts (in the example in FIG. 1, a right ear and a left ear) of a body of the same user and has a function of measuring biological information of the user.

In addition, each of the first measurement apparatus 10A and the second measurement apparatus 10B transmits the measured biological information to an information collection terminal 3. For example, a wearable terminal, a smartphone, a tablet terminal, a personal computer, and a server computer can be applied as the information collection terminal 3. The number of measurement apparatuses comprised in the measurement system 1 according to the present embodiment may be plural, and is not limited to two as illustrated in FIG. 1 and may be greater than or equal to three. Hereinafter, the first measurement apparatus 10A and the second measurement apparatus 10B will be simply referred to as "measurement apparatuses 10" unless otherwise distinguished.

FIG. 2 illustrates an example of a part on which each measurement apparatus 10 is mounted, an example of a form of each measurement apparatus, and a part of a measurement target of each measurement apparatus 10. As illustrated in FIG. 2, each measurement apparatus 10 measures the biological information in at least one of an artery or a vein of the user. Here, for example, the biological information measured by the measurement apparatuses 10 from the artery and the vein is at least one of a pulse (a pulse waveform and/or a pulse rate) or an arterial blood oxygen saturation level (SpO2). This biological information can be measured using, for example, photoplethysmography (PPG) that is a measurement method by irradiating a body surface of the user with light and measuring a change in blood flow rate that changes in accordance with pulsation of a heart as an amount of change in light. For example, this biological information is used in diagnoses of various diseases such as arterial embolism, aneurysm, diabetes, and economy class syndrome.

In addition, as illustrated in FIG. 2, each of the first measurement apparatus 10A and the second measurement apparatus 10B may measure the biological information in parts of left-right symmetry of the body of the user. For example, as illustrated in FIG. 1, in a case where the first measurement apparatus 10A and the second measurement apparatus 10B of earphone types are mounted on the right ear and the left ear, respectively, the biological information in external carotid arteries in left and right two locations is measured. In addition, as illustrated in FIG. 2, each of the first measurement apparatus 10A and the second measurement apparatus 10B may measure the biological information in upstream and downstream sides (for example, an external carotid artery and a common carotid artery) of a blood vessel branch of the user.

In such a manner, measuring the biological information from a plurality of different parts and performing a comprehensive diagnosis based on a measurement result enable an abnormality that is difficult to be discovered with only the biological information measured from one part to be found. For example, comparing a pulse waveform measured from the external carotid arteries in the left and right two locations enables an embolus that has occurred in only one of the external carotid arteries to be found. However, the measurement result of the biological information reflects health states and states of various diseases at the moment and thus, is considered to change depending on a timing of measurement. Accordingly, in a case of measuring the biological information from the plurality of different parts and using the biological information in the diagnosis, it is desired to improve accuracy of the diagnosis by synchronizing the timing of measuring the biological information in each part. Therefore, the first measurement apparatus 10A and the second measurement apparatus 10B according to the present embodiment measure the biological information of the user by synchronizing the timing with each other. Hereinafter, detailed configurations of the first measurement apparatus 10A and the second measurement apparatus 10B will be described.

Figure 3:
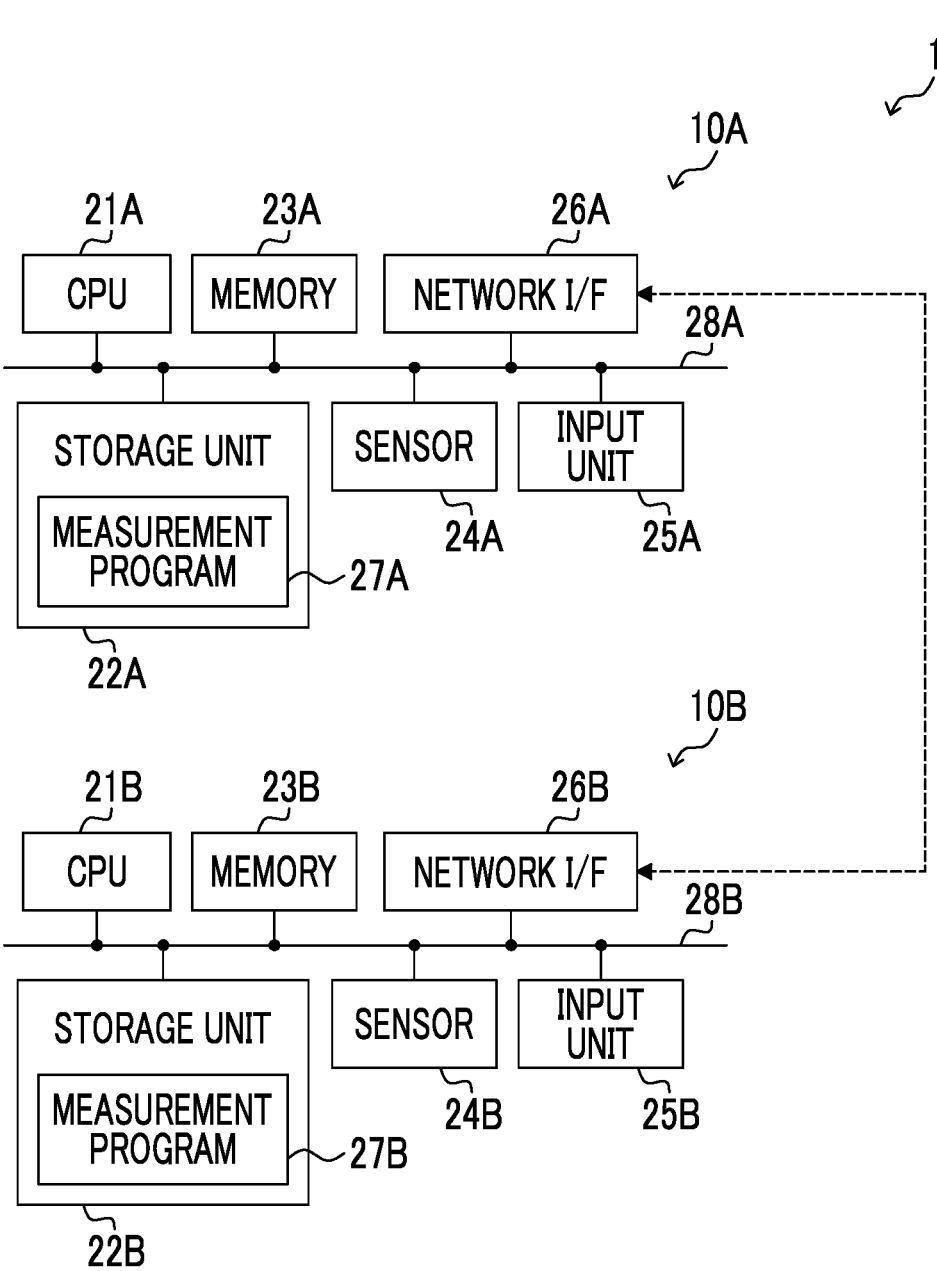
FIG. 3 is a block diagram illustrating an example of hardware configurations of a first measurement apparatus and a second measurement apparatus.

First, an example of hardware configurations of the first measurement apparatus 10A and the second measurement apparatus 10B according to the present embodiment will be described with reference to FIG. 3. As illustrated in FIG. 3, the first measurement apparatus 10A includes a central processing unit (CPU) 21A, a non-volatile storage unit 22A, and a memory 23A as a transitory storage region. In addition, the first measurement apparatus 10A includes a sensor 24A, an input unit 25A such as a button, and a network interface (I/F) 26A.

The storage unit 22A is implemented by, for example, a storage medium such as a hard disk drive (HDD), a solid state drive (SSD), and a flash memory. The storage unit 22A stores a measurement program 27A in the first measurement apparatus 10A. The CPU 21A loads the measurement program 27A into the memory 23A by reading out the measurement program 27A from the storage unit 22A and executes the loaded measurement program 27A. The sensor 24A is a sensor that irradiates the body surface with light and measures light reflected inside a living body using, for example, photodiodes or phototransistors. The network I/F 26A performs wired or wireless communication with another measurement apparatus 10 (for example, the second measurement apparatus 10B), the information collection terminal 3, and an external network (not illustrated).

The CPU 21A, the storage unit 22A, the memory 23A, the sensor 24A, the input unit 25A, and the network I/F 26A are connected to be capable of exchanging various information with each other through a bus 28A such as a system bus and a control bus. The CPU 21A is an example of a first processor according to the embodiment of the present disclosure. For example, various wearable terminals (refer to FIG. 2) of the earphone type, a glasses type, a wristwatch type, a supporter type, and a wear type can be applied as the first measurement apparatus 10A.

As illustrated in FIG. 3, the second measurement apparatus 10B includes a CPU 21B, a storage unit 22B, a memory 23B, a sensor 24B, an input unit 25B, and a network I/F 26B. Functions and configurations of these constituents are the same as those designated by the same reference numerals (only "A" and "B" at the end are different) as the first measurement apparatus 10A and thus, will not be described. The CPU 21B is an example of a second processor according to the embodiment of the present disclosure.

Figure 4:
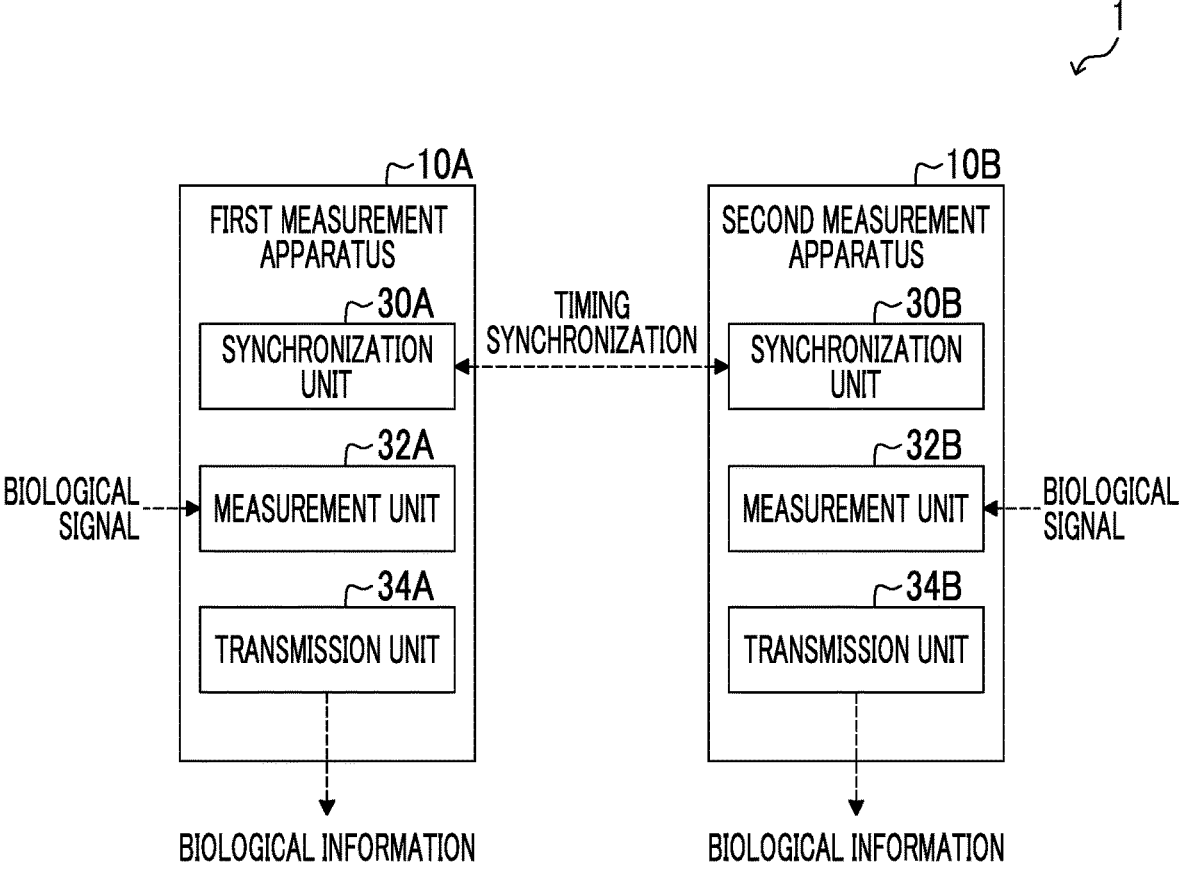
FIG. 4 is a block diagram illustrating an example of functional configurations of the first measurement apparatus and the second measurement apparatus.

Next, an example of functional configurations of the first measurement apparatus 10A and the second measurement apparatus 10B according to the present embodiment will be described with reference to FIG. 4. As illustrated in FIG. 4, the first measurement apparatus 10A includes a synchronization unit 30A, a measurement unit 32A, and a transmission unit 34A. The CPU 21A functions as the synchronization unit 30A, the measurement unit 32A, and the transmission unit 34A by executing the measurement program 27A. Similarly, the second measurement apparatus 10B includes a synchronization unit 30B, a measurement unit 32B, and a transmission unit 34B. The CPU 21B functions as the synchronization unit 30B, the measurement unit 32B, and the transmission unit 34B by executing a measurement program 27B.

The synchronization unit 30A and the synchronization unit 30B synchronize the timing related to the measurement of the biological information with each other using wired or wireless communication. Specifically, first, in a case where a state where the measurement of the biological information can be performed is set, the synchronization unit 30A and the synchronization unit 30B transmit a signal indicating the state to each other through the network I/F 26A and the network I/F 26B. The "state where the measurement of the biological information can be performed" is, for example, a state where the sensor 24A and the sensor 24B are appropriately mounted on parts of the body of the user and can acquire biological signals. After the state where the measurement of the biological information can be performed is checked with each other, the synchronization unit 30A and the synchronization unit 30B transmit and receive a synchronization signal indicating the timing of measuring the biological information by the measurement unit 32A and the measurement unit 32B (details will be described later) to and from each other through the network I/F 26A and the network I/F 26B.

Here, a specific example of synchronizing the timing by the synchronization unit 30A and the synchronization unit 30B will be described with reference to FIG. 5. FIG. 5 is a diagram illustrating a measurement period of the biological information of the user by each of the first measurement apparatus 10A and the second measurement apparatus 10B as a rectangle, in which a horizontal axis denotes time. FIG. 5 illustrates nine types of variations of Patterns 1 to 9 in accordance with a method of synchronization by the synchronization unit 30A and the synchronization unit 30B. In addition, FIG. 5 illustrates the timing of synchronization by the synchronization unit 30A and the synchronization unit 30B by a bold line. As illustrated in each pattern in FIG. 5, the synchronization unit 30A and the synchronization unit 30B synchronize the timing at least once.

For example, as illustrated in Patterns 1 to 4 in FIG. 5, the synchronization unit 30A and the synchronization unit 30B may synchronize with each other with respect to at least one of a start timing or an end timing of the measurement period. Pattern 1 is a diagram in which the timing is synchronized such that the entire measurement period matches (that is, both of the start timing and the end timing of the measurement period match). Pattern 2 is a diagram in which the timing is synchronized such that the start timing of the measurement period matches. Pattern 3 is a diagram in which the timing is synchronized such that the end timing of the measurement period matches. Pattern 4 is a diagram in which the timing is synchronized such that the end timing of the measurement period by the first measurement apparatus 10A matches the start timing of the measurement period by the second measurement apparatus 10B.

In addition, for example, as illustrated in Patterns 5 to 7 in FIG. 5, the synchronization unit 30A and the synchronization unit 30B may synchronize the timing with each other in at least a part of the measurement period of the biological information of the user. Pattern 5 is a diagram in which the timing is synchronized such that the measurement period by the second measurement apparatus 10B starts within the measurement period by the first measurement apparatus

10A. Pattern 6 is a diagram in which the timing is synchronized within the measurement period by the first measurement apparatus 10A and the measurement period by the second measurement apparatus 10B. Pattern 7 is a diagram in which the timing is synchronized such that a time interval between the start timing of the measurement period by the second measurement apparatus 10B that starts the measurement later, and the end timing of the measurement period by the first measurement apparatus 10A that finishes the measurement earlier is a predetermined interval t7.

In addition, for example, as illustrated in Patterns 8 and 9 in FIG. 5, the synchronization unit 30A and the synchronization unit 30B may synchronize the timing with a predetermined time difference from each other. Pattern 8 is a diagram in which the timing is synchronized such that the start timing of the measurement period by the second measurement apparatus 10B is after a predetermined time difference t8 from the start timing of the measurement period by the first measurement apparatus 10A. Pattern 9 is a diagram in which the timing is synchronized such that the start timing of the measurement period by the second measurement apparatus 10B is after a predetermined time difference t9 from the end timing of the measurement period by the first measurement apparatus 10A.

Which of each pattern illustrated in FIG. 5 is to be employed for the synchronization by the synchronization unit 30A and the synchronization unit 30B may be predetermined for each measurement target part (refer to FIG. 2) of the biological information and may be stored in the storage unit 22A and the storage unit 22B.

The measurement unit 32A measures the biological information of the user at the timing synchronized by the synchronization unit 30A. Specifically, the measurement unit 32A measures the biological information (for example, the pulse and SpO2) by analyzing the biological signal (indicates, for example, intensity of the light reflected inside the living body) of the user detected by the sensor 24A. Similarly, the measurement unit 32B measures the biological information of the user at the timing synchronized by the synchronization unit 30B. Specifically, the measurement unit 32B measures the biological information by analyzing the biological signal of the user detected by the sensor 24B.

The transmission unit 34A transmits the biological information measured by the measurement unit 32A to the information collection terminal 3 by wired or wireless communication through the network I/F 26A. Similarly, the transmission unit 34B transmits the biological information measured by the measurement unit 32B to the information collection terminal 3 by wired or wireless communication through the network I/F 26B.

Figure 6:
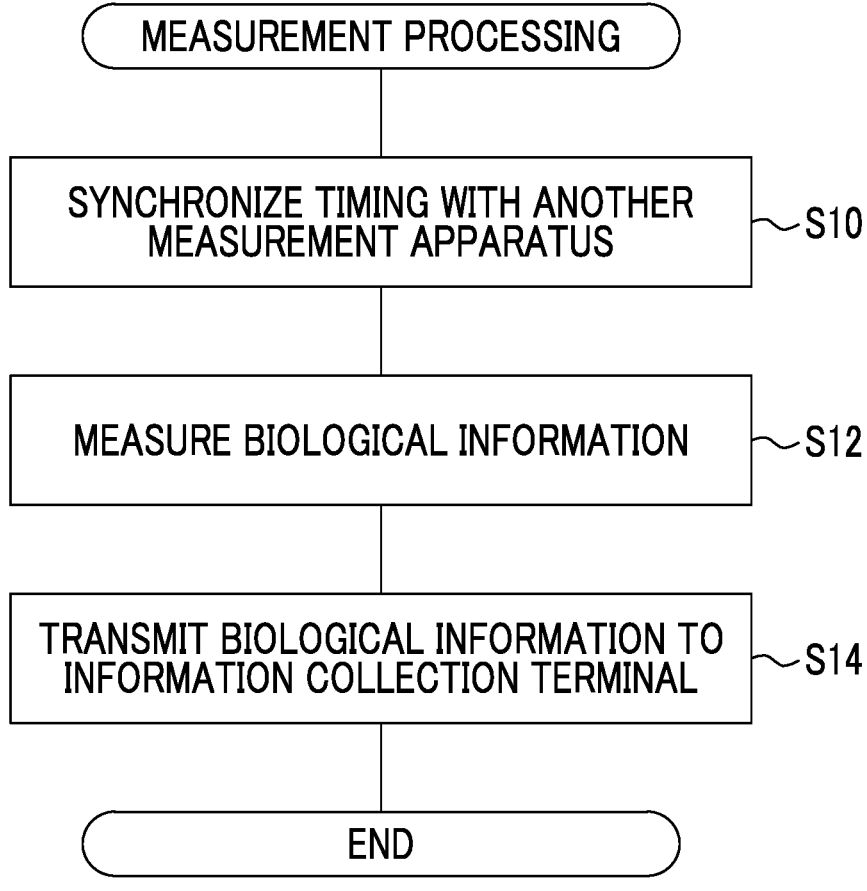
FIG. 6 is a flowchart illustrating an example of measurement processing.

Next, actions of the first measurement apparatus 10A and the second measurement apparatus 10B according to the present embodiment will be described with reference to FIG. 6. In the first measurement apparatus 10A, measurement processing illustrated in FIG. 6 is executed by executing the measurement program 27A by the CPU 21A. For example, the measurement processing may be executed in a case where an execution start instruction is provided by the user through the input unit 25A, or may be executed in a case where the state where the measurement of the biological information can be performed is set (even in a case where an instruction is not particularly provided).

In step S10, the synchronization unit 30A synchronizes the timing with the synchronization unit 30B in the second measurement apparatus 10B (another measurement apparatus). In step S12, the measurement unit 32A measures the biological information of the user at the timing synchronized by the synchronization unit 30A in step S10. In step S14, the transmission unit 34A transmits the biological information measured by the measurement unit 32A to the information collection terminal 3 and finishes the present measurement processing.

Similarly, even in the second measurement apparatus 10B, the same processing as the measurement processing illustrated in FIG. 6 is executed by executing the measurement program 27B by the CPU 21B. The measurement processing in the second measurement apparatus 10B is the same as the measurement processing in the first measurement apparatus 10A except that a counterpart of the synchronization in step S10 is the synchronization unit 30A of the first measurement apparatus 10A, and thus, will not be described.

As described above, the measurement system 1 comprises the first measurement apparatus 10A comprising at least the CPU 21A and the second measurement apparatus 10B comprising at least the CPU 21B. The CPU 21A and the CPU 21B measure the biological information of the user by synchronizing the timing with each other. That is, according to the measurement system 1 according to the present embodiment, even in a case of measuring the biological information in each of a plurality of parts of the body of the user, the timing of measurement can be synchronized. Thus, the accuracy of the diagnosis based on the biological information can be improved.

In the embodiment, the number of measurement apparatuses comprised in the measurement system 1 is not limited to two (the first measurement apparatus 10A and the second measurement apparatus 10B) as illustrated in FIG. 1 and may be greater than or equal to three as described above (refer to FIG. 2). In a case where the measurement system 1 comprises three or more measurement apparatuses, all of the measurement apparatuses comprised in the measurement system 1 may not synchronize the timing with each other, and at least two measurement apparatuses may synchronize the timing with each other.

For example, in a case where the measurement system 1 further comprises a third measurement apparatus comprising at least a third processor, at least two out of the CPU 21A comprised in the first measurement apparatus 10A, the CPU 21B comprised in the second measurement apparatus 10B, and the third processor may measure the biological information of the user by synchronizing the timing with each other. In addition, for example, when a predetermined number (for example, more than half) of measurement apparatuses are set in the state where the measurement of the biological information can be performed among all of the measurement apparatuses comprised in the measurement system 1, the measurement apparatuses in the state where the measurement can be performed may start measuring the biological information by synchronizing the timing with each other.

In addition, in the embodiment, the measurement apparatus 10 may be an apparatus that can be mounted on an existing earphone, glasses, wristband, supporter, wear, and the like in any manner by an adhesive or the like. In this case, the measurement apparatus 10 may have a function of sensing on which part of the body of the user the measurement apparatus 10 is mounted. For example, a well-known method using an acceleration sensor can be applied as a method of implementing such a function.

In addition, in the embodiment, a part or all of each measurement apparatus 10 and the information collection terminal 3 may be an integrated device. For example, the first measurement apparatus 10A and the information collection terminal 3 may be configured as the same wristwatch type wearable terminal (smartwatch), and the second measurement apparatus 10B may be configured as another device.

In addition, in the embodiment, the measurement apparatus 10 may search for the other measurement apparatus 10 that measures the biological information of the same user, and in a case where the other measurement apparatus 10 is detected, may measure the biological information of the user by synchronizing the timing with the other measurement apparatus 10. For example, a well-known method using short range wireless communication such as Bluetooth (registered trademark) can be applied as a method of implementing such a function.

In addition, in the embodiment, for example, the following various processors can be used as a hardware structure of a processing unit that executes various processing of the synchronization units 30A and 30B, the measurement units 32A and 32B, and the transmission units 34A and 34B. The various processors include, in addition to the CPU that is a general-purpose processor functioning as various processing units by executing software (program) as described above, a programmable logic device (PLD) such as a field programmable gate array (FPGA) that is a processor having a circuit configuration changeable after manufacturing, a dedicated electric circuit such as an application specific integrated circuit (ASIC) that is a processor having a circuit configuration dedicatedly designed to execute specific processing, and the like.

One processing unit may be configured with one of the various processors or may be configured with a combination of two or more processors of the same type or different types (for example, a combination of a plurality of FPGAs or a combination of a CPU and an FPGA). In addition, a plurality of processing units may be configured with one processor.

Examples of the plurality of processing units configured with one processor include, first, as represented by a computer such as a client and a server, a form in which one processor is configured with a combination of one or more CPUs and software, and the processor functions as the plurality of processing units. Second, as represented by a system on chip (SoC) or the like, a form of using a processor that implements functions of the entire system including the plurality of processing units by one integrated circuit (IC) chip is included. In such a manner, various processing units are configured using one or more of the various processors as a hardware structure.

Furthermore, more specifically, an electric circuit (circuitry) in which circuit elements such as semiconductor elements are combined can be used as the hardware structure of the various processors.

In addition, in the embodiment, while an aspect in which the measurement program 27A is stored (installed) in advance in the storage unit 22A, and the measurement program 27B is stored (installed) in advance in the storage unit 22B is described, the present disclosure is not limited thereto. The measurement program 27A and the measurement program 27B may be provided in the form of a recording on a recording medium such as a compact disc read only memory (CD-ROM), a digital versatile disc read only memory (DVD-ROM), and a universal serial bus (USB) memory. In addition, the measurement program 27A and the measurement program 27B may be in the form of being downloaded from an external apparatus through a network. Furthermore, in addition to the program, the disclosed technology is applied to a storage medium that stores the program in a non-transitory manner.

In the disclosed technology, the examples of the embodiment can also be appropriately combined. Above described contents and illustrated contents are detailed description for parts according to the embodiment of the disclosed technology and are merely an example of the disclosed technology. For example, description related to the above configurations, functions, actions, and effects is description related to an example of configurations, functions, actions, and effects of the parts according to the embodiment of the disclosed technology. Thus, unnecessary parts may be removed, new elements may be added, or parts may be replaced in the above described contents and the illustrated contents without departing from the gist of the disclosed technology.

What is claimed is:

1. A measurement system comprising:
a first measurement apparatus including at least a first processor and a first sensor, operation of the first sensor being controlled by the first processor; and
a second measurement apparatus including at least a second processor and a second sensor, operation of the second sensor being controlled by the second processor,
wherein the first sensor and the second sensor are configured to measure biological information of different parts of a body of a user during at least a part of a measurement period of the biological information,
wherein a timing of the operation of the first sensor and a timing of the operation of the second sensor are synchronized, and
wherein the first sensor is configured to measure the biological information in a left part of the user's body and the second sensor is configured to measure the biological information in a right part of the user's body, the left part and the right part being a pair of body parts that share a left-right symmetry.

2. The measurement system according to claim 1, wherein the first sensor and the second sensor are configured to end operation at the same time.

3. The measurement system according to claim 1, wherein the first sensor and the second sensor are configured to operate at a predetermined time difference from each other.

4. The measurement system according to claim 1, wherein each of the first sensor and the second sensor is configured to measure the biological information in upstream and downstream sides of a blood vessel branch of the user.

5. The measurement system according to claim 1, wherein each of the first sensor and the second sensor is configured to measure the biological information in at least one of an artery or a vein of the user.

6. The measurement system according to claim 1, wherein the biological information is at least one of a pulse or an arterial blood oxygen saturation level.

7. The measurement system according to claim 1, wherein wireless communication is used to control the timing of synchronization between the first sensor and the second sensor.

8. The measurement system according to claim 1, further comprising:
a third measurement apparatus including at least a third processor and a third sensor, operation of the third sensor being controlled by the third processor.

* * * * *